(12) United States Patent  
Osypka (10) Patent No.: US 7,585,190 B2
(45) Date of Patent: Sep. 8, 2009

(54) ELECTRICAL CONNECTOR AND DEVICES USING THE SAME

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 0 days.

(21) Appl. No.: 12/228,574

(22) Filed: Aug. 14, 2008

(65) Prior Publication Data

US 2008/0311772 A1 Dec. 18, 2008

Related U.S. Application Data

(62) Division of application No. 11/342,032, filed on Jan. 27, 2006, now Pat. No. 7,422,487.

(51) Int. Cl.
*H01R 24/04* (2006.01)
(52) U.S. Cl. .......................... 439/668; 439/68; 439/909
(58) Field of Classification Search ................. 439/668, 439/669, 86, 909
See application file for complete search history.

(56) References Cited

U.S. PATENT DOCUMENTS

| | | | |
|---|---|---|---|
| 2,749,526 A | 6/1956 | Petersen | |
| 3,546,657 A | 12/1970 | Cook | |
| 4,712,557 A | 12/1987 | Harris | |
| 5,070,605 A | 12/1991 | Daglow et al. | |
| 5,358,409 A | 10/1994 | Obara | |
| 5,376,206 A | 12/1994 | Maurer et al. | |
| 5,676,694 A | 10/1997 | Boser et al. | |
| 6,912,423 B2 | 6/2005 | Ley et al. | |
| 2003/0162422 A1* | 8/2003 | Sobhani | 439/86 |
| 2005/0070140 A1* | 3/2005 | Gelman | 439/86 |
| 2005/0272280 A1 | 12/2005 | Osypka | |

\* cited by examiner

*Primary Examiner*—Hien Vu
(74) *Attorney, Agent, or Firm*—Scott D. Wofsy; Edwards Angell Palmer & Dodge LLP (57) ABSTRACT

The subject disclosure is directed to female connectors which can be employed in a quick connect/disconnect system used in medical devices to provide a non-permanent electrical and mechanical engagement with a male connector. The female connectors include, inter alia, a connector body that has an outer periphery and an aperture extending therethrough. The connector body has a flexible, non-conductive portion and a conductive portion which is at least partially exposed in the aperture and on the outer periphery of the connector body. The connector body is constructed such that when a male connector is inserted into the aperture of the connector body, the flexible, non-conductive part and the conductive part of the connector body cooperate to allow for expansion of the aperture, creating contact pressure between the conductive part of the connector body and the male connector.

13 Claims, 5 Drawing Sheets

ELECTRICAL CONNECTOR AND DEVICES USING THE SAME

CROSS REFERENCE TO RELATED APPLICATIONS

This Application is a Divisional Application of U.S. patent application Ser. No. 11/342,032, filed Jan. 27, 2006, which application is incorporated herein by reference in its entirety.

This application claims priority to U.S. Provisional Patent Application Ser. No. 60/647,736, filed Jan. 27, 2005, entitled "CONNECTING MECHANISM FOR USE WITH A MALE CONNECTOR," and to U.S. patent application Ser. No. 11/179,304, filed Jun. 12, 2005, entitled "LEAD ADAPTER HAVING LOW RESISTANCE CONDUCTORS AND/OR ENCAPSULATED HOUSING," the disclosures of each of these applications are herein incorporated by reference their entirety.

BACKGROUND OF THE INVENTION

1. Field of the Invention

The subject invention is directed generally to electro-mechanical connecting mechanisms, and more particularly, to electrical connectors that are configured for providing a non-permanent mechanical engagement and electrical communication with male connectors typically associated with leads used in electrophysiological devices, such as implantable cardiac rhythm management devices and external electrical generators.

2. Background of the Related Art

Electrical stimulation devices for cardiac stimulation are well known in the medical field. Cardiac stimulation devices are used for therapeutic and/or diagnostic purposes. These devices, which include cardiac pacemakers and implantable cardiac defibrillators, generally interface with cardiac tissue by means of implantable or otherwise attachable cardiac leads. These leads employ male connectors to operatively connect with matching receptacles located in the therapeutic and/or diagnostic devices.

Connectors are available in various configurations which are often of standardized types readily recognized by those practicing in the art. Common connector types well known in the art currently include: IS-1 type (International Standard ISO 5841.3:2000) low profile pacing/sensing connectors which have a 3.2 mm diameter and are available in unipolar or bipolar configurations; LV-1 type pacing/sensing connectors which have a 1.8 mm diameter and are available in unipolar and bipolar configurations (Guidant Corporation); and DF-1 type (International Standard ISO 11318:2002) defibrillator connectors which have a unipolar configuration.

There is a need for a quick connect/disconnect female connector system that is adapted to receive male connectors, such as the aforementioned standardized connectors, and provides a secure, non-permanent mechanical engagement therewith.

SUMMARY OF THE INVENTION

The subject disclosure is directed to female connectors which can be employed in a quick connect/disconnect system used in medical devices to provide a non-permanent electrical and mechanical engagement with a male connector. The female connector includes, inter alia, a connector body that has an outer periphery and an aperture extending therethrough. In certain embodiments, the connector body is cuboid (i.e., a rectangular parallelepiped). Moreover, in representative embodiments, the aperture formed in the connector body has a circular cross-section when viewed in a plane extending perpendicularly through its central axis.

The connector body includes a flexible, non-conductive portion and a conductive portion which is at least partially exposed in the aperture and on the outer periphery of the connector body. The connector body is constructed such that when a male connector is inserted into the aperture of the connector body, the flexible, non-conductive part and the conductive part of the connector body cooperate to allow for expansion of the aperture, creating contact pressure between the conductive part of the connector body and the male connector.

Preferably, the conductive portion of the connector body is more rigid than the non-conductive portion of the connector body. Moreover, in certain embodiments, the conductive portion of the connector body includes two or more conductive segments. In constructions which include two conductive segments, the conductive segments can be positioned on diametrically opposing sides of the aperture defined through the connector body. Still further, the conductive portion of the connector body can include interlocking conductive segments which in combination define the aperture and are free to move radially with respect to each other.

It is presently preferred that in certain embodiments of the disclosed female connector, at least a portion of the aperture formed in the connector body is defined by the flexible, non-conductive portion of the connector body. Alternatively, the conductive portion of the connector body can define the entire inner diametrical surface of the aperture. In certain constructions, a plurality of circumferentially spaced, axially extending grooves can be formed in the inner diametrical surface of the aperture.

It is envisioned that the conductive portion of the connector body can be made from materials, such as, titanium, 316L stainless steel or MP35N, or combinations thereof. In a representative embodiment, the conductive portion of the connector body is made from a nonmagnetic, nickel-cobalt-chromium-molybdenum alloy. Moreover, the non-conductive portion of the connector body is preferably made from silicon. It is also envisioned that the connector body is made using an over-molded process and/or an injection molding process.

The present disclosure is also directed to a female connector for use with a male connector having an outer diameter. The female connector includes a connector body that has an outer periphery and defines a through aperture. The connector body includes a flexible, non-conductive portion and a conductive portion, which is at least partially exposed in the aperture and on the outer periphery of the connector body. The connector body is constructed such that when the outer diameter of the male connector is larger than the inner diameter of the aperture, the flexible, non-conductive part and conductive part of the connecter body cooperate to allow for expansion of the aperture and receipt of the male connector and create contact pressure between the conductive part of the connector body and the male connector.

The subject invention is also directed to an electrical adapter for receiving at least one male connector. The adapter includes, inter alia, a housing and at least one female connector disposed within a receptacle defined by the housing. The receptacle(s) defined by the housing are configured for receiving a male connector(s). The female connector includes a connector body that has an outer periphery and aperture extending through the body. In certain embodiments, the connector body is cuboid (i.e., a rectangular parallelepiped). Moreover, it is presently envisioned that in representative embodiments, the aperture has a circular cross-section when viewed in a plane extending perpendicularly through its central axis.

The connector body is formed from a flexible, non-conductive portion and a conductive portion. The non-conductive portion is at least partially exposed in the aperture and on the outer periphery of the connector body. The connector body is constructed such that when a male connector is inserted into the aperture of the connector body, the flexible, non-conductive part and the conductive part of the connector body cooperate to allow for expansion of the aperture, creating contact pressure between the conductive part of the connector body and the male connector.

In a preferred embodiment, the adapter includes, inter alia, a plurality of female connectors coaxially positioned within the receptacle of the housing and axially spaced apart. Each female connector is adapted for electrical communication with a surface electrode provided on the male connector. It is presently envisioned that the housing is made substantially from electrically non-conductive material.

In certain embodiments, the aperture in the female connector has an inside diameter which is preferably at least partially smaller than the outside diameter of the male connector. Therefore, insertion of the male connector into the aperture causes a force to be exerted on the periphery of the aperture and female connector in general. The flexible and resilient non-conductive portion of the connector body deflects or deforms in response, thus allowing the opening to be enlarged only as much as sufficient to permit the male connector to be fully extended through the opening. Due to its resiliency, the non-conductive portion reacts in a spring-like manner to the deformation, and a corresponding resistive force urges the aperture to return to its original configuration (i.e., prior to deformation). The resistive force directed toward the aperture results in the formation of a non-permanent mechanical engagement with the conductive portion of the connector body which is exposed in the aperture and the male connector.

The subject disclosure is also directed to a system for receiving a male connector having a plurality of surface electrodes spaced apart and exposed along the periphery of the male connector. The system of the present invention can be incorporated in a variety of equipment and devices, such as pacemakers and neuro-stimulators, or devices of other types from diverse fields.

The housing for the disclosed female connector can be separate from a particular device, such as an adapter, or part of a device, such as a pacemaker (e.g., the header cavity). The housing can also include the remaining components required for the particular device to function. The system also includes one or more electrically conductive lines for providing electrical communication between the conductive portions of the female connectors and features, components, further connectors or whatever appropriate destinations are associated with the device.

These and other aspects of the female connectors and systems of the subject invention will become more readily apparent from the following description taken in conjunction with the drawings.

BRIEF DESCRIPTION OF THE DRAWINGS

So that those having ordinary skill in the art to which the subject invention pertains will more readily understand how to make and use the female connector of the subject invention, preferred embodiments thereof will be described in detail hereinbelow with reference to the drawings, wherein.

DETAILED DESCRIPTION OF THE PREFERRED EMBODIMENTS

Referring now to the drawings wherein like reference numerals identify similar structural elements of the subject invention, there is illustrated in FIGS. 1-8 exemplary embodiments of female connectors which have been constructed in accordance with the present disclosure. The exemplary female connectors presented herein are all generally rectangular shaped blocks (i.e., cuboids) with a circular opening or aperture defined approximately at the center of the larger side face. However, connecting mechanisms constructed according to the present disclosure, along with any openings therein, can be of a variety of other shapes and configurations without departing from the inventive aspects of the present application.

Figure 1:
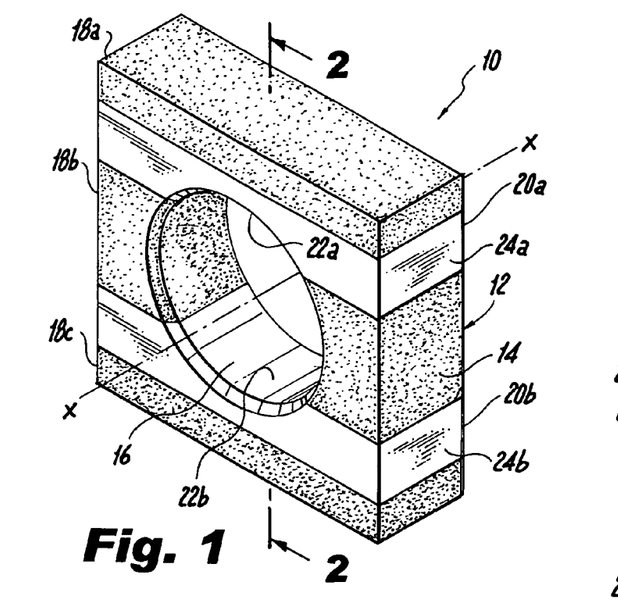
FIG. 1 is a perspective view of a female connector which has been constructed in accordance with a preferred embodiment of the present invention.
Figure 2:
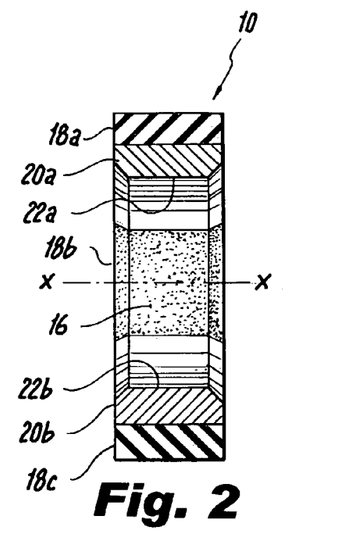
FIG. 2 is a cross-sectional view taken along axis 2-2 of the female connector of FIG. 1.

Referring now to FIGS. 1 and 2, there is illustrated a female connector which has been constructed in accordance with the present invention and designated by reference numeral 10. Female connector 10 includes a connector body 12 that has an outer periphery 14 and an aperture 16 extending therethrough. Connector body 12 is cuboid (i.e., a rectangular parallelepiped) and the aperture 16 formed in the connector body has a circular cross-section when viewed in a plane extending perpendicularly through central axis "X".

Connector body 12 includes flexible, non-conductive segments 18a-c and diametrically opposed conductive segments 20a and 20b. Each of the conductive segments 20a/20b include a inner surface, 22a and 22b, respectively, which is exposed in the aperture 16. Each of the conductive portions 20a/20b also have a surface, 24a and 24b, respectively, which is exposed on the outer periphery 14 of the connector body 12. Connector body 12 is constructed such that when a male connector is inserted into aperture 16 of the connector body 12, the flexible, non-conductive segments 18a-18c and the conductive segments 20a and 20b of the connector body 12 cooperate to allow for expansion of the aperture 16, creating contact pressure between the surfaces 24a and 24b of conductive parts 20a and 20b of the connector body 12 and the male connector.

In the presently disclosed embodiment, the conductive segments 20a and 20b of the connector body 12 are more rigid than the non-conductive segments 18a-18c. In the embodiment disclosed in FIGS. 1 and 2, the conductive segments 20a and 20b are made from MP35N, a nonmagnetic, nickel-cobalt-chromium-molybdenum alloy. Moreover, the non-conductive segments 18-18c of the connector body 12 are made from silicon. Connector body 12 is made by positioning the conductive segments 20-20b within a mold and over-molding the segments with injected silicon rubber.

Upon insertion of a male connector, electrically non-conductive segments 18a-18c deflect or deform radially outward which permits passage of the larger diameter male connector through aperture 16. However, the resilient character of non-conductive segments 18a-18c respond by exerting a radially inward force to urge surfaces 22a and 22b of conductive segments 20a and 20b against electrodes located on the surface of the male connector.

Figure 3:
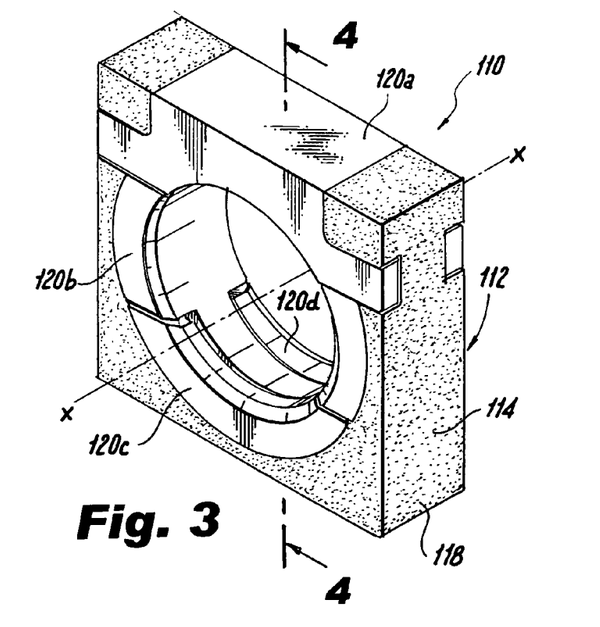
FIG. 3 is a perspective view of a female connector which has been constructed in accordance with a second preferred embodiment of the present invention.
Figure 4:
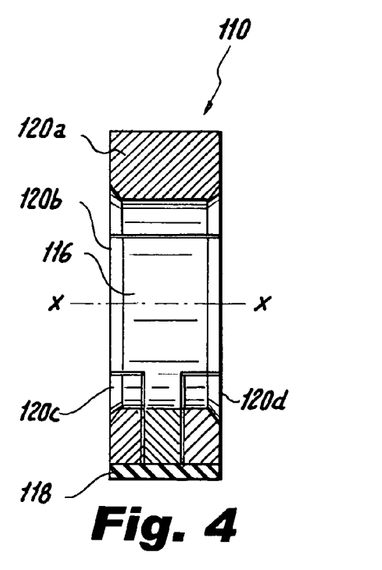
FIG. 4 is a cross-sectional view taken along axis 4-4 of the female connector shown in FIG. 3.

With reference now to FIGS. 3 and 4, there is illustrated a second exemplary embodiment of a female connector that has been constructed in accordance with the present disclosure and designated by reference numeral 110. Like female connector 10, connector 110 includes a connector body 112 that has an outer periphery 114 and an aperture 116 extending therethrough. Moreover, connector body 112 is cuboid and the aperture 116 formed in the connector body has a circular cross-section when viewed in a plane extending perpendicularly through central axis "X".

Also like the previously described female connector 10, connector body 112 of connector 110 is formed from a flexible, non-conductive portion which has been molded around a conductive portion. The electrically conductive portion of the connector body includes conductive segments 120a, 120b, 120c and 120d which are positioned adjacent to the perimeter of aperture 116 with non-conductive portion 118 positioned generally on the radially outer volume of connector body 112. Upon insertion of a male connector, the arrangement of the conductive segments 120a-120d allows each of the segments to move radially outward and relative to each other, thereby expanding the inside diameter of aperture 116. The non-conductive portion 118 of the connector body 112 is sufficiently flexible to allow for the radial movement of the conductive segments 120a-120e, but in response thereto the non-conductive segment 118 exerts a reactive force onto conductive portions 120a-120d, resulting in a secure mechanical engagement with the male connector and electrical engagement with electrodes on the male connector.

Figure 5:
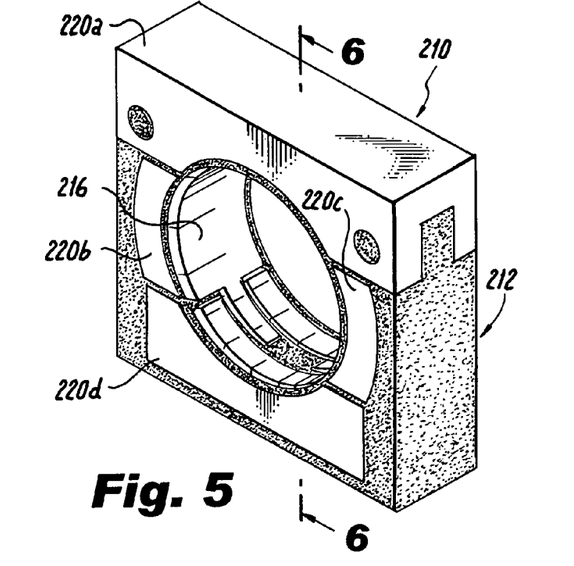
FIG. 5 is a perspective view of a yet further embodiment of a female connector which has been constructed in accordance with the present invention.
Figure 6:
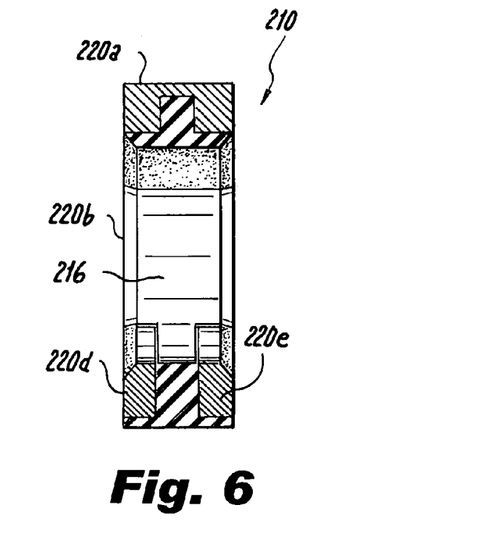
FIG. 6 is a cross-sectional view taken along axis 6-6 of the female connector shown in FIG. 5.
Figure 7:
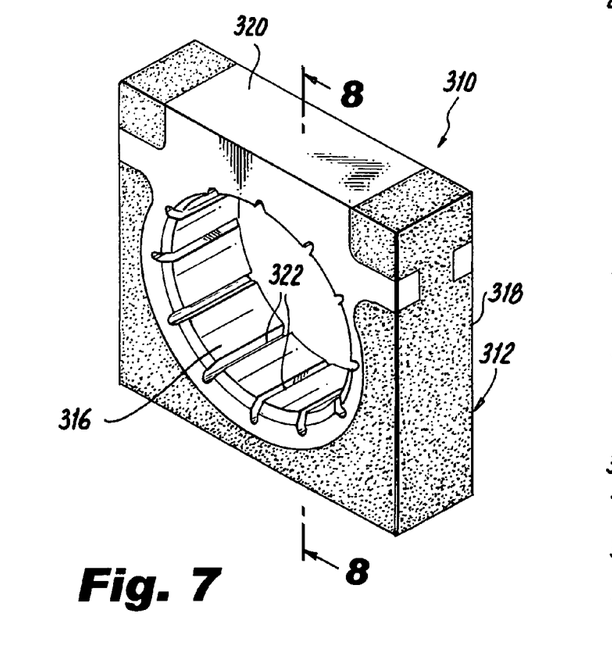
FIG. 7 is a perspective view of a female connector which has been constructed in accordance with a fourth preferred embodiment of the present invention.

With reference now to FIGS. 5 and 6, which illustrate a third exemplary embodiment of a female connector which has been constructed in accordance with the present disclosure and designated by reference numeral 210. Like the previously described female connectors 10 and 110, connector 210 includes a connector body 212 that has an outer periphery 214 and an aperture 216 extending therethrough. Additionally, connector body 212 is cuboid and the aperture 216 formed in the connector body has a circular cross-section when viewed in a plane extending perpendicularly through central axis "X".

Still further, connector body 212 of connector 210 is formed from a flexible, non-conductive portion which has been molded around a conductive portion. The flexible non-conductive portion 218 is generally positioned around the lower periphery of the connector body 212. The conductive portion of the connector body 212 includes conductive segments 220a-220e which are positioned adjacently with respect to each other in a generally interdigitated configuration and separated by non-conductive portion 218. Upon insertion of a male connector, the arrangement of the conductive segments 120a-120e allows each of the segments to move radially outward and relative to each other, thereby expanding the inside diameter of aperture 216. The non-conductive portion 218 of the connector body 212 is sufficiently flexible to allow for the radial movement of the conductive segments 220a-220e, but in response thereto the non-conductive segment 218 exerts a reactive force onto conductive portions 120a-120e, resulting in a mechanical engagement with the male connector and electrical engagement with electrodes on the male connector.

Figure 8:
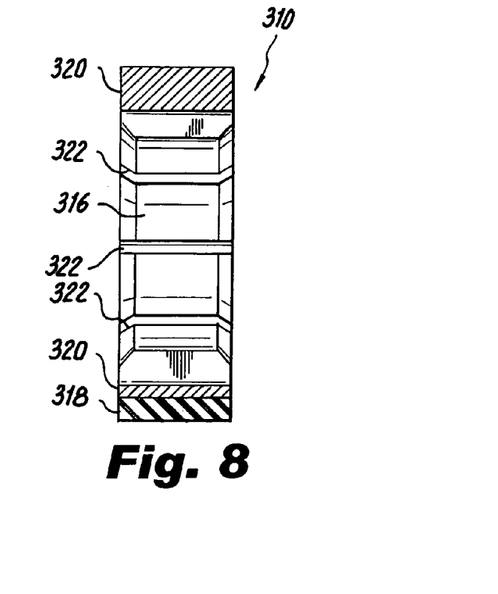
FIG. 8 is a cross-sectional view taken along axis 8-8 of the female connector shown in FIG. 7.
Figure 9:
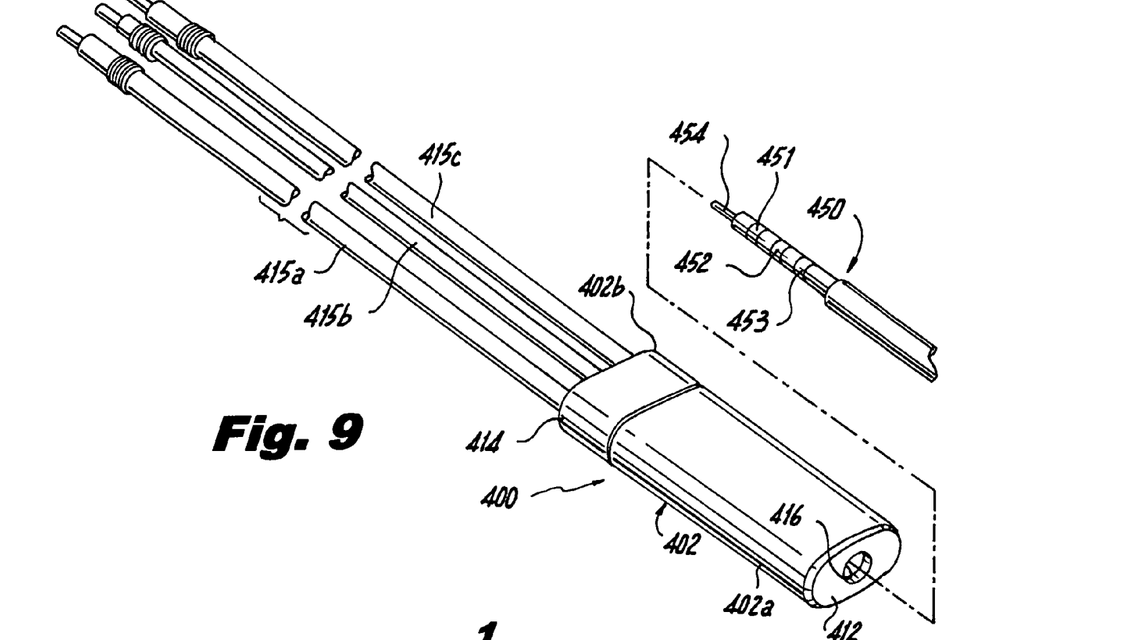
FIG. 9 is a perspective view of a lead having a male connector associated with an end thereof and a lead adapter which has been constructed in accordance with the teachings of the present invention.

With reference now to FIGS. 8 and 9, there is illustrated a fourth exemplary embodiment of a female connector which has been designated as reference numeral 310 and is constructed in accordance with the present disclosure. Female connector 310 includes an electrically conductive portion 320 disposed substantially around the periphery of aperture 316. Conductive portion 320 includes a plurality of circumferentially-spaced, axially-extending grooves 322 on an interior periphery thereof that facilitate radial flexing of conductive portion 320. It should be noted that conductive portion 320 can also be made from a material which exhibits some pliability, although it is not required.

Upon insertion of a male connector, the grooves 322 and flexibility of the material allow conductive portion 320 to deform and expand the inside diameter of aperture 316. Moreover, the non-conductive portion 318 of the connector body 312 is sufficiently flexible to allow for the radially outward movement of conductive portion 320, but in response thereto the non-conductive segment 318 exerts a reactive force onto conductive portion 320, resulting in a mechanical engagement with the male connector and secure electrical engagement with electrodes on the male connector.

Although any conductive material can be used for electrically conductive portions in accordance with the present disclosure, the exemplary embodiments described herein preferably employ titanium, 316L Stainless Steel, or MP35N. Any flexible and resilient non-conductive material may be used for the electrically non-conductive portion in accordance with the present disclosure, although silicone and like are presently preferred for the exemplary embodiments shown herein. Female connectors 10, 110, 210 and 310 are preferably made by an overmold process, such as a process which involves positioning the conductive portions in a desired configuration within a mold prior to the non-conductive material being injected therein.

With reference now to FIGS. 9-13, which illustrate a lead adapter for use with an electrophysical device which has been designated as reference numeral 400. Lead adapter 400 is an exemplary embodiment of a device which can incorporate the female connectors of the present invention to provide electrical communication and a non-permanent mechanical engagement between the various connector types associated with implantable cardiac rhythm management devices and external electrical generators.

Although lead adapter 400 is configured to mechanically and electrically engage male quadripolar connector 450 (e.g., DF-4 type) which has three electrode rings 451 (distal), 452 (medial), 453 (proximal) and a distal tip electrode 454, it should be readily apparent that female connectors constructed in accordance with the present invention can be used to provide a mechanical and electrical engagement in any system which utilizes a male connector having one or more surface electrodes.

Those skilled in the art will further appreciate that the quadripolar connector 450, while described herein by way of a non-limiting example as a DF-4 type connector, could be an IS-4 type quadripolar connector, designed for pacing and sensing, rather than defibrillation. In such instances, the connector 450 could have contact configurations such as IS4-LLLO or IS4-LLLL. Moreover, the adapter can be configured to accept other male connectors without departing from the inventive aspects of the present disclosure.

Lead adaptor 400 includes an encapsulated thermoplastic housing 410 which defines a proximal end portion 412 and a distal end portion 414. The proximal end portion 412 has a first receptacle 416 configured to receive a male connector 450 that associated with a first implantable cardiac lead. The receptacle 416 includes hardware, such as female connectors 456a-456c, for providing an electrical interface with surface electrodes associated with the cardiac lead connectors, as discussed in more detail below.

Elongated flexible leads 415a-415c extend from the distal end portion 414 of the adaptor housing 410. The leads 415a-415c are preferably formed from silicone or a similar biocompatible material.

Figure 10:
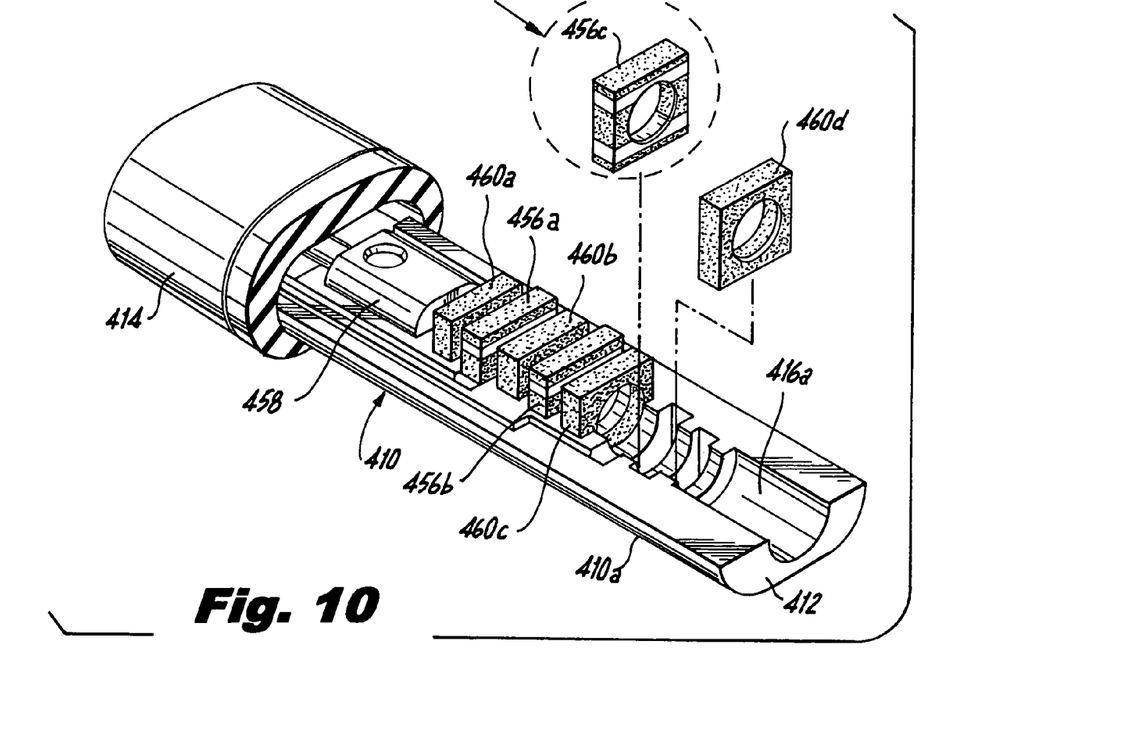
FIG. 10 is a partially exploded perspective view of the housing portion of the lead adapter of FIG. 9.
Figure 11:
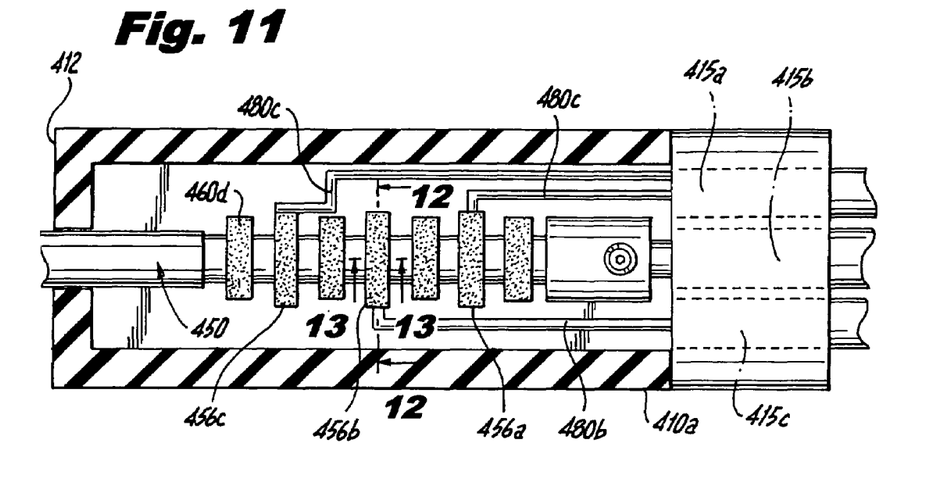
FIG. 11 is a plan view of the lead adapter of FIG. 9 with the upper half of the two-part adapter housing removed for ease of illustration.
Figures 12, 13:
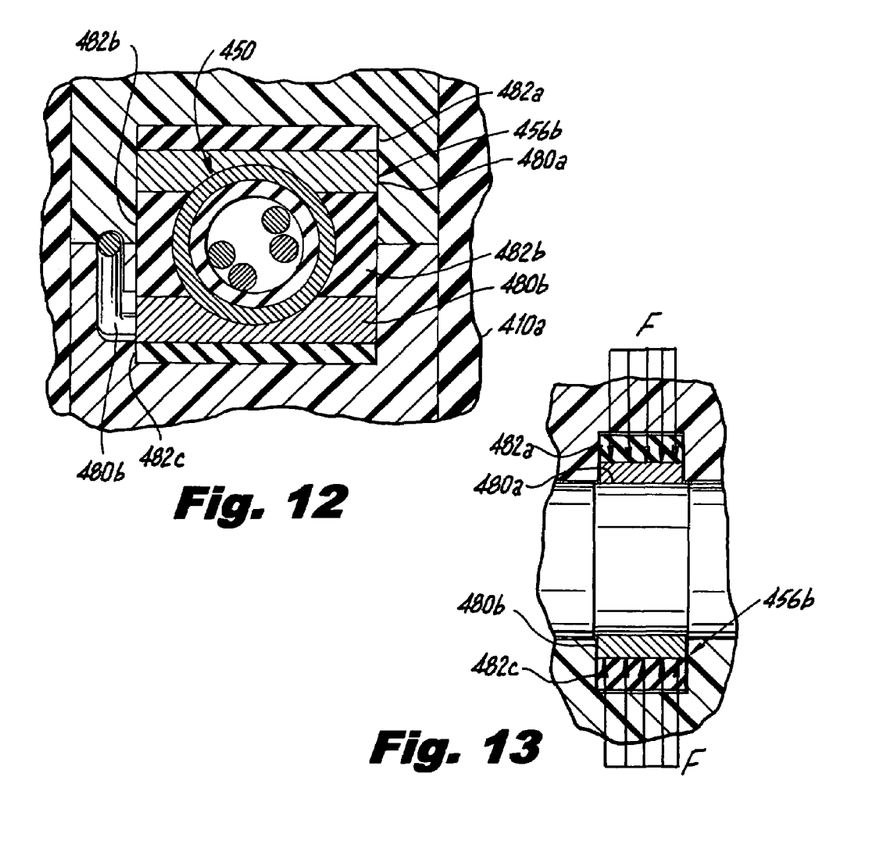
FIG. 12 is a cross-sectional view taken along axis 12-12 of the lead adapter of FIG. 11.
FIG. 13 is a cross-sectional view taken along axis 13-13 of the lead adapter of FIG. 11.

Referring now to FIGS. 9-11, adaptor housing 410 is a two-part structure (410a, 410b) having internal cavities that define or otherwise form the first receptacle 416 and accommodate the mechanical components and conductive wires associated therewith. The two halves 410a, 410b (not shown) of housing 410 fit together and add stability to the proximal receptacle portion 416 of adaptor housing 410. It also provides a means of easy assembly. Adaptor housing 410 is preferably constructed from a relatively stiff thermoplastic material, such as, for example, polyurethane, tecothane, polycarbonate and/or composites thereof.

Adaptor housing 410 is encapsulated or otherwise enclosed within a two-part outer hull section including a distal hull section 402a and a proximal hull section 402b. The hull sections 402a, 402b are formed from a biocompatible material, such as, for example, silicone or a similar material. The outer hull provides stability for the proximal receptacle portion 412 of the adaptor 400, while offering protection and seal for biocompatibility and long-term reliability. It is envisioned and well within the scope of the subject disclosure that instead of having two separate hull sections enclosing the adaptor housing 410, the housing 410 could be over-molded with the silicone outer hull after it has been assembled using molding techniques known in the art.

Receptacle 416 of adaptor housing 410 is configured for mechanical and electrical connection with a quadripolar connector of a cardiac lead, and in this exemplary case, a DF-4 type connector. Receptacle 416 includes a series of recesses or cavities that contain a plurality of electrical connectors 456 for accommodating the contacts of a four-pole lead connector 450. Theses female connectors include a distal pin connector 458 having an associated locking screw (not shown) which together receive and mechanically secure the distal connector pin 454 of quadripolar connector 450; a distal female connector 456a for receiving and electrically connecting with a distal contact ring 451 of a quadripolar connector 450; a medial female connector 856b for receiving and electrically connecting with a medial contact ring 452 of a quadripolar connector 450; and a proximal female connector 456c for receiving and electrically connecting with a proximal contact ring 453 of a quadripolar connector 450.

Female connectors 456a-456c are constructed in accordance with the present invention, as described above with reference to FIGS. 1-9. Accordingly, the connectors 456a-456c have uniquely designed conductive portions formed from a material such as titanium, 316L stainless steel or MP35N, which are over-molded with a resilient non-conductive material such as silicone that functions to provide a secure mechanical and electrical connection between the connectors and the contacts.

Insulating seals 460a-460d are disposed within a series of recesses defined in the receptacle 416 between adjacent ring contacts. These include a distal insulating seal 460a disposed between pin connector 458 and female connector 456a; a first medial insulating seal 460b disposed between female connectors 456a and 456b; a second medial insulating seal 460c disposed between female connectors 456b and 456c; and a proximal insulating seal 460d disposed proximal to female connector 456c adjacent the reception bore 416a of receptacle 416.

Adapter 400 includes an elongated, generally rectangular housing 422 having opposing proximal and distal ends 424 and 426, respectively. A mating or female connector cavity 428 is defined in proximal end 424 to extend distally within housing 422. A female electrode pin receiving port 430 is disposed in the distal end of cavity 428 for receiving the pin electrode 454 of quadripolar lead 450. As shown in FIG. 6, housing 422 is preferably fabricated as two elongated halves and made from an electrically non-conductive material.

In the representative embodiment disclosed in FIGS. 9-13, female connectors 456a-456c are constructed similar to female connector 10 of FIGS. 1 and 2, but could be constructed in accordance with alternative embodiment disclosed herein. More specifically, female connectors 456a-456c include a connector body that has an outer periphery and an aperture extending therethrough. The connector body of each of the connectors 456a-456c, includes flexible, non-conductive segments 482a-482c and diametrically opposed conductive segments 480a and 480b.

Connectors 456a-456c are constructed such that when a male connector 450 is inserted into receptacle 416 of adapter 400, the flexible, non-conductive segments and the conductive segments of the female connectors 456a-456c cooperate to allow for expansion of the aperture, creating contact pressure "F" (see FIG. 13) between the conductive segments of the female connectors and the male connector. More specifically, upon insertion of male connector 450, the electrically non-conductive segments of the female connectors deflect or deform radially outward which permits passage of the male connector 450 through receptacle 416. However, the resilient character of the non-conductive segments respond by exerting a radially inward force "F" to urge the conductive segments against the electrodes 451-453 located on the surface of the male connector 450.

As shown is FIG. 11, low resistance conductive wires 480a-480c connect the electrically conductive portion of female connectors 456a-456c to the components and leads positioned within the distal end portion 414 of the lead adapter 400.

Figure 14:
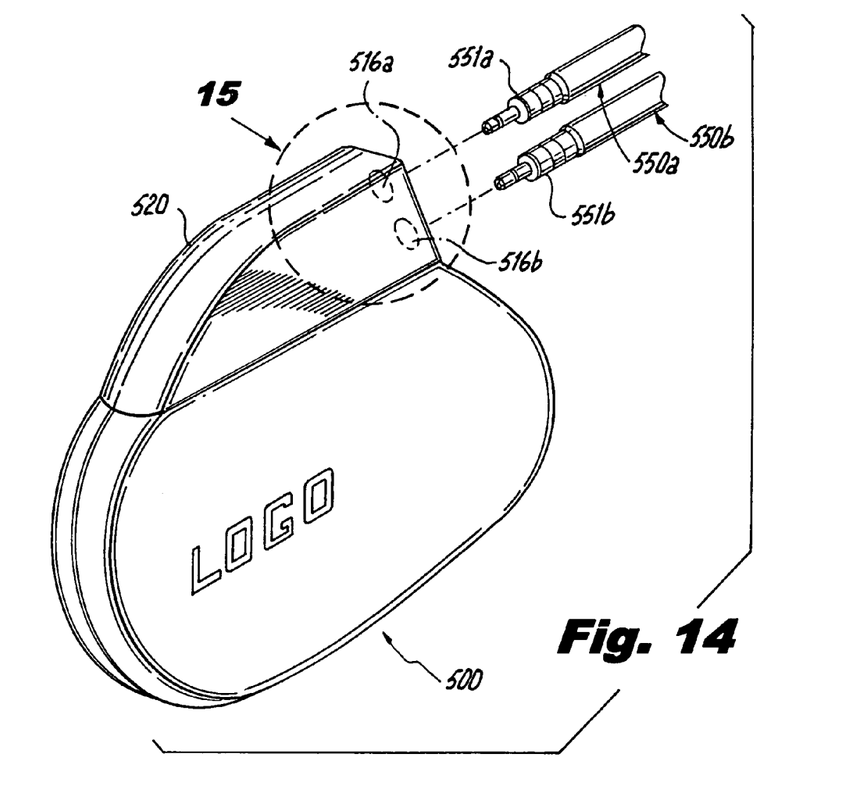
FIG. 14 is a perspective view of a pulse generating device having two receptacles for receiving two male connectors.
Figure 15:
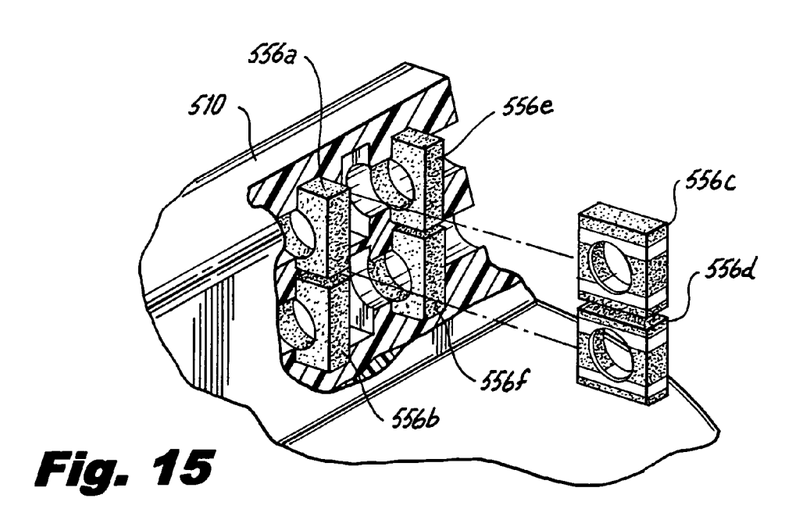
FIG. 15 is enlarged perspective view of the header cavity for the pulse generating device shown in FIG. 14.

Referring now to FIGS. 14 and 15, which illustrate a pulse generating device 500 that includes two receptacles 516a and 516b for receiving the male connectors 551a and 551b associated with electrical leads 550a and 550b. The receptacles 516a and 516b are formed in the header cavity 520 of pulse generating device 500. As shown in FIG. 15, each receptacle 516a and 516b includes three female connectors 556a-556f, which are constructed in accordance with the teachings of the present invention and operate as previously described.

While the subject invention of the present disclosure has been described with respect to preferred and exemplary embodiments, those skilled in the art will readily appreciate that various changes and/or modifications can be made to the invention without departing from the spirit or scope of the invention as described herein. It should also be readily apparent that the female connectors of the present invention can be used in the receptacles of many other devices, such as pacemakers, headers, defibrillators, neuro-stimulators, to connect, lock and unlock with male connectors.

What is claimed is:

1. A female connector for positioning in an insulated adapter housing, to receive a male connector, the female connector comprising: a connector body having an outer periphery and defining a through aperture having an inner periphery, the connector body including:
   a) a flexible, non-conductive portion and;
   b) a conductive portion, which at least partially defines the inner periphery of the aperture and the outer periphery of the connector body, the conductive portion being adapted and configured to expand radially outwardly upon insertion of the male connector therethrough, the connector body being constructed such that when the male connector is inserted through the aperture of the connector body, the flexible, non-conductive portion and the conductive portion of the connector body cooperate to allow for radially outward expansion of the aperture, resulting in radially inwardly directed contact pressure between the conductive portion of the inner periphery of the connector body and an outer periphery of the male connector;
   wherein the conductive portion of the connector body defines an inner diametrical surface of the aperture; and
   wherein the inner diametrical surface defined by the conductive portion of the connector body includes a plurality of circumferentially spaced, axially extending grooves.

2. A female connector as recited in claim 1, wherein the connector body is a cuboid.

3. A female connector as recited in claim 1, wherein the aperture has a circular cross-section when viewed in a plane extending perpendicularly through its central axis.

4. A female connector as recited in claim 1, wherein the conductive portion of the connector body is more rigid than the non-conductive portion of the connector body.

5. A female connector as recited in claim 1, wherein the conductive portion of the connector body includes two or more conductive segments.

6. A female connector as recited in claim 1, wherein at least a portion of the aperture is defined by the flexible, non-conductive portion of the connector body.

7. A female connector as recited in claim 1, wherein the conductive portion of the connector body is made from a material selected from the group consisting of titanium, 316L stainless steel or MP35N, and combinations thereof.

8. A female connector as recited in claim 1, wherein the conductive portion of the connector body is made from a nonmagnetic, nickel-cobalt-chromium-molybdenum alloy.

9. A female connector as recited in claim 1, wherein the non-conductive portion of the connector body is made from silicon.

10. A female connector as recited in claim 1, wherein the connector body is made using an over-molding process.

11. A female connector as recited in claim 1, wherein the connector body is made using an injection molding process.

12. A female connector for positioning in an insulated adapter housing to receive a male connector having an outer diameter, the female connector comprising: a connector body having an outer periphery and defining a through aperture having an inner periphery, the connector body including a flexible, non-conductive portion and a conductive portion which at least partially defines the inner periphery of the aperture and the outer periphery of the connector body, the conductive portion being adapted and configured to expand radially outwardly upon insertion of the male connector therethrough, the connector body being constructed such that when the outer diameter of the male connector is larger than the inner diameter of the aperture, the flexible, non-conductive part and conductive part of the connector body cooperate to allow for expansion of the aperture and receipt of the male connector and create contact pressure between the conductive portion of the connector body and the male connector;
   wherein the conductive portion of the connector body defines an inner diametrical surface of the aperture; and
   wherein the inner diametrical surface defined by the conductive portion of the connector body includes a plurality of circumferentially spaced, axially extending grooves.

13. A female connector as recited in claim 12, wherein the conductive portion of the connector body includes two or more conductive segments.

* * * * *